United States Patent [19]

Livey et al.

[11] Patent Number: 5,530,103

[45] Date of Patent: Jun. 25, 1996

[54] **METHOD FOR THE PURIFICATION OF PC PROTEIN FROM *BORRELIA BURGDORFERI***

[75] Inventors: Ian Livey; Friedrich Dorner, both of Vienna, Austria

[73] Assignee: Immuno Aktiengesellschaft, Vienna, Austria

[21] Appl. No.: 31,295

[22] Filed: Mar. 12, 1993

Related U.S. Application Data

[60] Division of Ser. No. 903,580, Jun. 25, 1992, which is a continuation-in-part of Ser. No. 824,161, Jan. 22, 1992, abandoned, which is a continuation-in-part of Ser. No. 727,245, Jul. 11, 1991, abandoned.

[51] Int. Cl.$^6$ .................... C07K 1/16; C07K 1/18; C07K 1/22
[52] U.S. Cl. ............. 530/416; 530/412; 530/415; 530/427; 530/825; 424/234.1
[58] Field of Search .................... 424/92, 234.1; 530/412, 415, 825, 416, 427

[56] References Cited

U.S. PATENT DOCUMENTS

| | | | |
|---|---|---|---|
| 4,721,617 | 1/1988 | Johnson | 424/234.1 |
| 4,888,276 | 12/1989 | Shelburne | 435/7.32 |
| 5,192,540 | 3/1993 | Kuo et al. | 424/190.1 |

FOREIGN PATENT DOCUMENTS

| | | |
|---|---|---|
| 252641 | 1/1988 | European Pat. Off. |
| 418827A1 | 3/1991 | Germany |
| 3942728C1 | 5/1991 | Germany |
| WO90/04411 | 3/1990 | WIPO |
| WO91/09870 | 7/1991 | WIPO |

OTHER PUBLICATIONS

Dunn et al Protein Expression & Purification 1: 159–168 1990.
Brandt et al, Infect & Immun. 58(4): 983–991, 1990.
Praec Mursic et al. *Infection*, 18: 332–341 (1990).
Barbour *Clin. Microbiol. Revs.*, 1(4): 399–414 (1988).
Barbour *Rev. Inf. Dis.*, 11(6): S1470–1474 (1989).
Bergstrom et al. *Mol. Microbiol.*, 3(4): 479–486 (1989).
Wilske et al. *N.Y. Acad. Sci.*, 539: 126–143 (1988).
Gassman et al. *Nuc. Acids Res.*, 17(9): 3590 (1989).
Simpson et al. *J. Clin. Microbiol.*, 28(6): 1329–1337 (1990).
Fuchs et al. Fourth Intern. Conference on Lyme Borreliosis (1990).
Wilske et al. *Zbl. Bakt. Hyg.*, 263: 92–102 (1986).
Hansen et al. *J. Clin. Microbiol.*, 26(2): 338–346 (1988).
Coleman et al. *J. Infect. Dis.*, 155(4): 756–765 (1987).
Wilske et al. Fourth Intern. Conf. on Lyme Borreliosis (1990).
Fikrig et al. *Science*, 250: 553–556 (1990).
Regenmortel *Immunology Today*, 10(8): 226–272 (1989).
Simpson et al, National Technical Info. Service Accession #PB90–206376, U.S. patent application Ser. No. 07/487,716, filed Mar. 5, 1990 Published by Dept. of Health & Human Services.
Schaible et al. *PNAS, U.S.A.*, 87: 3768–3772 (1990).
Steere *The New England Journal of Medicine*, 321(9): 586–596 (1989).
Luft et al. *Infection and Immunity*, 57(11): 3637–3645 (1989).
Wilske *J. of Infectious Diseases*, 153(2): 304–314 (1986).
German Patent Application, Max Plankt Institute, published Mar. 19, 1991.
Berzofsky et al. "Protein Antigenic Structures Recognized by T Cells: Potential Applications to Vaccine Design", *Immunological Reviews*, 98: 9–52 (1987).
Simon et al. "A mouse model for *Borrelia burgdorferi* infection: approach to a vaccine against Lyme disease", *Immunology Today*, 12(1): 12–16 (1991).
Simpson et al. National Technical Info. Service Accession #PB90441144, U.S. patent application Ser. No. 07/427,735, filed Oct. 26, 1989 Published by Natl Inst. Heath.
Doward et al, National Technical Info Service Accession #PB90–213018, U.S. patent application Ser. No. 07/485,551 filed Feb. 27, 1990. Published by Natl. Inst. Health.
Schwan et al, National Technical Info. Service Accession #PB90–134841, U.S. Patent Application 07/361,850 filed Jun. 5, 1989, published by Dept of Health & Human Services.
*Data For Biochemical Research* 3rd Edition, Dawson et al eds. Clarendon Press, Oxford, 1987 p. 287.
Cull et al, "Preparation of Extracts from Prokaryotes" in Methods in Enzymology 182: 147–153, 1990.
England et al, "Precipitation Techniques" in Methods in Enzymology 182: 285–300, 1990.
Gondolf et al J. of Chromatography 521:325–334, 1990.
Gabay et al, J. Bacteriology 162(1): 85–91, 1985.
Benz R. Crit Rev. Biochem 19:145–190, 1985.
Helenius et al Biochimica et Biophysica Acta 415: 24–79, 1975.
Wilske et al, Res Microbiol, 143: 583–596, 1992.

*Primary Examiner*—James C. Housel
*Assistant Examiner*—Julie Krsek-Staples
*Attorney, Agent, or Firm*—Foley & Lardner

[57] ABSTRACT

A method of purifying *B. burgdorferi* proteins comprising the steps of (a) disrupting a *B. burgdorferi* cell and fractionating the disrupted cell into membrane and cytoplasmic components; (b) resuspending the membrane component in a non-denaturing detergent thereby producing a solubilized protein and an insolubilized material and then separating said solubilized protein from said insolubilized material; (c) subjecting the solubilized protein to ion-exchange chromatography so as to produce protein fractions; and (d) assaying the protein fractions to identify those fractions which contain proteins of interest wherein the purified proteins of interest are in a biologically active form suitable for use in vaccines, is disclosed.

1 Claim, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 639 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Borrelia burgdorferi
        ( B ) STRAIN: Orth-1

( i x ) FEATURE:
        ( A ) NAME/KEY: CDS
        ( B ) LOCATION: 1..639

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AAA | AAG | AAT | ACA | TTA | AGT | GCG | ATA | TTA | ATG | ACT | TTA | TTT | TTA | TTT | 48 |
| Met | Lys | Lys | Asn | Thr | Leu | Ser | Ala | Ile | Leu | Met | Thr | Leu | Phe | Leu | Phe | |
| 1 | | | | 5 | | | | | 10 | | | | | 15 | | |
| ATA | TCT | TGT | AAT | AAT | TCA | GGG | AAA | GGT | GGA | GAT | TCT | GCA | TCT | ACT | AAT | 96 |
| Ile | Ser | Cys | Asn | Asn | Ser | Gly | Lys | Gly | Gly | Asp | Ser | Ala | Ser | Thr | Asn | |
| | | | 20 | | | | | 25 | | | | | 30 | | | |
| CCT | GCT | GAC | GAG | TCT | GCG | AAA | GGA | CCT | AAT | CTT | ACA | GAA | ATA | AGC | AAA | 144 |
| Pro | Ala | Asp | Glu | Ser | Ala | Lys | Gly | Pro | Asn | Leu | Thr | Glu | Ile | Ser | Lys | |
| | | 35 | | | | | 40 | | | | | 45 | | | | |
| AAA | ATT | ACA | GAT | TCT | AAT | GCA | TTT | GTA | CTG | GCT | GTT | AAA | GAA | GTT | GAG | 192 |
| Lys | Ile | Thr | Asp | Ser | Asn | Ala | Phe | Val | Leu | Ala | Val | Lys | Glu | Val | Glu | |
| | 50 | | | | | 55 | | | | | 60 | | | | | |
| ACT | TTG | GTT | TCA | TCT | ATA | GAT | GAA | CTT | GCT | ACT | AAA | GCT | ATT | GGT | AAA | 240 |
| Thr | Leu | Val | Ser | Ser | Ile | Asp | Glu | Leu | Ala | Thr | Lys | Ala | Ile | Gly | Lys | |
| 65 | | | | | 70 | | | | | 75 | | | | | 80 | |
| AAA | ATA | CAA | CAA | AAT | AAT | GGT | TTA | GGC | GCC | AAT | GCG | GAT | AAA | AAC | GGA | 288 |
| Lys | Ile | Gln | Gln | Asn | Asn | Gly | Leu | Gly | Ala | Asn | Ala | Asp | Lys | Asn | Gly | |
| | | | | 85 | | | | | 90 | | | | | 95 | | |
| TCA | TTG | TTA | GCA | GGA | GCT | TAT | GCA | ATA | TCA | ACC | CTA | ATA | ACA | GAA | AAA | 336 |
| Ser | Leu | Leu | Ala | Gly | Ala | Tyr | Ala | Ile | Ser | Thr | Leu | Ile | Thr | Glu | Lys | |
| | | | 100 | | | | | 105 | | | | | 110 | | | |
| TTA | AAG | GCA | TTG | AAA | AAT | TCA | GGA | GAA | TTA | AAG | GCA | AAA | ATT | GAA | GAT | 384 |
| Leu | Lys | Ala | Leu | Lys | Asn | Ser | Gly | Glu | Leu | Lys | Ala | Lys | Ile | Glu | Asp | |
| | | 115 | | | | | 120 | | | | | 125 | | | | |
| GCT | AAG | AAA | TGT | TCT | GAA | GAT | TTT | ACT | AAA | AAA | CTA | GCT | GCT | GGG | CAT | 432 |
| Ala | Lys | Lys | Cys | Ser | Glu | Asp | Phe | Thr | Lys | Lys | Leu | Ala | Ala | Gly | His | |
| | 130 | | | | | 135 | | | | | 140 | | | | | |
| GCA | CAG | CTT | GGT | ATA | GAC | GGA | GCT | ACT | GAT | AAT | GAT | TCA | AAA | GAA | GCA | 480 |
| Ala | Gln | Leu | Gly | Ile | Asp | Gly | Ala | Thr | Asp | Asn | Asp | Ser | Lys | Glu | Ala | |
| 145 | | | | | 150 | | | | | 155 | | | | | 160 | |
| ATT | TTG | AAA | ACA | AAT | GGG | ACT | AAA | ACT | AAG | GGT | GCT | GAA | GAA | CTT | GTA | 528 |
| Ile | Leu | Lys | Thr | Asn | Gly | Thr | Lys | Thr | Lys | Gly | Ala | Glu | Glu | Leu | Val | |
| | | | | 165 | | | | | 170 | | | | | 175 | | |
| AAG | TTA | TCT | GAA | TCA | GTA | GCA | AGC | TTG | TCA | AAA | GCG | GCT | CAA | GAA | GCA | 576 |
| Lys | Leu | Ser | Glu | Ser | Val | Ala | Ser | Leu | Ser | Lys | Ala | Ala | Gln | Glu | Ala | |
| | | | 180 | | | | | 185 | | | | | 190 | | | |
| TCA | GCT | AAT | TCA | GTT | AAA | GAG | CTT | ACA | AGT | CCT | GTT | GTA | GCA | GAA | ACT | 624 |
| Ser | Ala | Asn | Ser | Val | Lys | Glu | Leu | Thr | Ser | Pro | Val | Val | Ala | Glu | Thr | |
| | | 195 | | | | | 200 | | | | | 205 | | | | |
| CCA | AAA | AAA | CCT | TAA | | | | | | | | | | | | 639 |
| Pro | Lys | Lys | Pro | | | | | | | | | | | | | |
| 210 | | | | | | | | | | | | | | | | |

( 2 ) INFORMATION FOR SEQ ID NO:2:

( i ) SEQUENCE CHARACTERISTICS:
        ( A ) LENGTH: 212 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Lys | Asn | Thr | Leu | Ser | Ala | Ile | Leu | Met | Thr | Leu | Phe | Leu | Phe |
| 1 | | | | 5 | | | | | 10 | | | | | 15 | |
| Ile | Ser | Cys | Asn | Asn | Ser | Gly | Lys | Gly | Gly | Asp | Ser | Ala | Ser | Thr | Asn |
| | | | 20 | | | | | 25 | | | | | 30 | | |
| Pro | Ala | Asp | Glu | Ser | Ala | Lys | Gly | Pro | Asn | Leu | Thr | Glu | Ile | Ser | Lys |
| | | 35 | | | | | 40 | | | | | 45 | | | |
| Lys | Ile | Thr | Asp | Ser | Asn | Ala | Phe | Val | Leu | Ala | Val | Lys | Glu | Val | Glu |
| | 50 | | | | | 55 | | | | | 60 | | | | |

| | | | | | | | | | | | | | | |
|---|---|---|---|---|---|---|---|---|---|---|---|---|---|---|
| Thr | Leu | Val | Ser | Ser | Ile | Asp | Glu | Leu | Ala | Thr | Lys | Ala | Ile | Gly | Lys |
| 65 | | | | | 70 | | | | | 75 | | | | | 80 |

| | | | | | | | | | | | | | | |
|---|---|---|---|---|---|---|---|---|---|---|---|---|---|---|
| Lys | Ile | Gln | Gln | Asn | Asn | Gly | Leu | Gly | Ala | Asn | Ala | Asp | Lys | Asn | Gly |
| | | | | 85 | | | | | 90 | | | | | 95 | |

| | | | | | | | | | | | | | | |
|---|---|---|---|---|---|---|---|---|---|---|---|---|---|---|
| Ser | Leu | Leu | Ala | Gly | Ala | Tyr | Ala | Ile | Ser | Thr | Leu | Ile | Thr | Glu | Lys |
| | | | 100 | | | | | 105 | | | | | 110 | | |

| | | | | | | | | | | | | | | |
|---|---|---|---|---|---|---|---|---|---|---|---|---|---|---|
| Leu | Lys | Ala | Leu | Lys | Asn | Ser | Gly | Glu | Leu | Lys | Ala | Lys | Ile | Glu | Asp |
| | | 115 | | | | | 120 | | | | | 125 | | | |

| | | | | | | | | | | | | | | |
|---|---|---|---|---|---|---|---|---|---|---|---|---|---|---|
| Ala | Lys | Lys | Cys | Ser | Glu | Asp | Phe | Thr | Lys | Lys | Leu | Ala | Ala | Gly | His |
| | 130 | | | | | 135 | | | | | 140 | | | | |

| | | | | | | | | | | | | | | |
|---|---|---|---|---|---|---|---|---|---|---|---|---|---|---|
| Ala | Gln | Leu | Gly | Ile | Asp | Gly | Ala | Thr | Asp | Asn | Asp | Ser | Lys | Glu | Ala |
| 145 | | | | | 150 | | | | | 155 | | | | | 160 |

| | | | | | | | | | | | | | | |
|---|---|---|---|---|---|---|---|---|---|---|---|---|---|---|
| Ile | Leu | Lys | Thr | Asn | Gly | Thr | Lys | Thr | Lys | Gly | Ala | Glu | Glu | Leu | Val |
| | | | | 165 | | | | | 170 | | | | | 175 | |

| | | | | | | | | | | | | | | |
|---|---|---|---|---|---|---|---|---|---|---|---|---|---|---|
| Lys | Leu | Ser | Glu | Ser | Val | Ala | Ser | Leu | Ser | Lys | Ala | Ala | Gln | Glu | Ala |
| | | | 180 | | | | | 185 | | | | | 190 | | |

| | | | | | | | | | | | | | | |
|---|---|---|---|---|---|---|---|---|---|---|---|---|---|---|
| Ser | Ala | Asn | Ser | Val | Lys | Glu | Leu | Thr | Ser | Pro | Val | Val | Ala | Glu | Thr |
| | | 195 | | | | | 200 | | | | | 205 | | | |

| | | | |
|---|---|---|---|
| Pro | Lys | Lys | Pro |
| | 210 | | |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

ATTAAGGTTT TTTTGGAGTT TCTG 24

METHOD FOR THE PURIFICATION OF PC PROTEIN FROM *BORRELIA BURGDORFERI*

This application is a division of application Ser. No. 07/903,580, filed Jun. 25, 1992 which is a continuation-in-part of application Ser. No. 07/824,161 filed Jan. 22, 1992, now abandoned, which is a continuation-in-part of application Ser. No. 07/727,245 filed Jul. 11, 1991, now abandoned.

BACKGROUND OF THE INVENTION

The present invention relates to the prevention of Lyme disease in mammals. More specifically, the invention relates to immunogenic formulations and to methods for using them to retard or prevent the development of Lyme disease.

The phrases "Lyme disease" and "Lyme borreliosis" generically denote tick-borne infections caused by the spirochaete *Borrelia burgdorferi*, representing the most common tick-transmitted disease in both the United States and Europe. Lyme disease is similar to syphilis because it affects many organs, most commonly the skin, nervous system, heart and joints, and because it develops in stages and may become chronic.

Since Lyme disease may mimic other diseases, a need exists for -accurate diagnostic tools, especially in difficult cases where the clinical picture is inconclusive. There is also a need for methods to treat or prevent the disease. Antibiotic therapy may be effective if initiated soon after infection, but prolonged, high dosage treatment is necessary once the disease has progressed. Moreover, antibiotic therapy is not always successful. See Preac Mursic et al., *Infection* 18: 332–341 (1990). Accordingly, a vaccine to prevent Lyme disease is desirable.

Several antigens of *B. burgdorferi* are known. Two major outer-surface proteins of *B. burgdorferi*, ospA (31 kd) and ospB (34 kd), are discussed by Barbour, *Clin. Microbiol. Revs.* 1:399–414 (1988). OspA is present in most strains but is heterogeneous; that is, ospA proteins from different strains may differ in molecular weight and in serological reactivity.

OspB is less widely distributed among strains than ospA but, like ospA, exists in different serological and molecular weight forms. The genes for ospA and ospB, which are plasmid-encoded, have been cloned, sequenced, and expressed in *E. coli*. See Barbour, et al., *Rev. Inf. Dis.* 11(6): S1470–74 (1989); Bergström, et al., *Mol. Microbiol.* 3:479–86 (1989).

The pC (24 kd) protein of *B. burgdorferi* is similar to ospA and B in some respects. It, too is a lipoprotein and exhibits molecular weight and serological heterogeneity and is exposed on the cell-surface (it is available on the cell-surface to bind agglutinating antibody and cell-associated pC is susceptible to digestion by proteases). Strains expressing pC protein are common in Europe. Between 40% to 50 % of the 28 European isolates tested by Wilske, et al., *N.Y. Acad. Sci.* 539:126–43 (1988), were positive for the pC protein, although this may be an underestimate because pC expression is subject to fluctuations.

Other *B. burgdorferi* antigens include the outer-surface protein found in the 60 kd region, Barbour, et al., supra; the flagellar structural protein in the 41 kd region, Gassmann, et al., *Nucleic Acids Res.* 17:3590 (1989); the protein of the 39 kd region, Simpson, et al., *J. Clin. Micro.* 28: 1329–37 (1990); and an approximately 94 kd protein, Fuchs, et al., FOURTH INTERNATIONAL CONFERENCE ON LYME BORRELIOSIS (1990).

Various purification methods have been used in preparing antigens for further study and characterization in this context. For instance, Wilske, et al., *Zbl. Bakt. Hyg.* 263:92–102 (1986), subjected whole Borreliae to a SDS-PAGE regimen in which the proteins were denatured by heat and exposure to the detergent sodium dodecyl sulphate (SDS) and 2-mercaptoethanol. Hansen, et al., *J. Clin. Microbiol.* 26(2): 338–46 (1988), disclosed the purification of *B. burgdorferi* flagellum. World Patent Application No. 90/04411 by Bergström, et al. teaches a non-denaturing method for partially purifying fractions of *Borrelia burgdorferi*.

Studies have also focused on the preparation and characterization of various antigens for purposes of developing diagnostic tests. Thus, a diagnostic procedure for detecting *B. burgdorferi* indirectly, by assaying for specific antibody production in response to infection, is disclosed in the aforementioned application of Bergström, et al., and in U.S. patent application Ser. No. 07/487,716 (Simpson & Schwan) (published Jul. 18, 1990).

Coleman, et al., *J. Infect. Dis.* 155:756–65 (1987), also disclose the production of a *B. burgdorferi* fractions by treating whole spirochaetes with denaturing SDS detergent, thereby to obtain a protoplasmic cylinder (the bacterium stripped of protein coat) fraction which, upon further treatment, can be employed as an antigen.

Wilske, et al., FOURTH INTERNATIONAL CONFERENCE ON LYME BORRELIOSIS (1990), report identifying immunodominant Borreliae proteins which are said to be useful in diagnosing Lyme borreliosis. These investigators conclude that two proteins, pC and p100, may be particularly important to the extent that they provide an indication of early and late stages of the disease, respectively.

Although various antigens are known, protective efficacy cannot be predicted from an antigen's ability to elicit an immune response in the course of a natural or experimental infection. For instance, the 41kd flagellar induces an immune response but is not protective. See Simon, et al., *Immunology Today* 12:11–16 (1991). The 94 kd protein similarly fails to provide protection, as reported below in Example 3. In fact, applicants have observed that antigens which are protective are relatively rare. Consequently, a large part of the immune response will be to antigens which are not relevant for protection. Conversely, some potentially protective antigens may fail to elicit an adequate immune response. Thus, utility as a vaccine constituent cannot be inferred from the ability of an antigen to elicit an antibody response.

Therefore, a need exists for continued research in the development of a suitable vaccine against Lyme borreliosis. Of interest in this regard is U.S. Pat. No. 4,721,617 (Johnson), which discloses a vaccine against Lyme borreliosis comprised of whole *B. burgdorferi* cells which had been inactivated by lyophilization. Based on recovery of the pathogen from kidney or spleen, Johnson demonstrates a dose-dependent reduction in the susceptibility of immunized hamsters to infection by a virulent *B. burgdorferi* strain. The effect was short-lived, however, and animals challenged 90 days post-vaccination were incompletely protected.

European Patent Application No. 418827 (Simon, et al.) describes a vaccine against *B. burgdorferi*, especially strains B31 or ZS7, comprised of monoclonal antibodies which recognize the 31 kD ospA protein. According to the aforementioned European application of Simon, et al., passive immunization of SCID-mice with these antibodies inhibits the development of Borrelia-induced symptoms. (Protection is defined in terms of resistance to infection and to the development of arthritis.) The European application also discloses expression in *E. coli* of a recombinant β-galactosidase/ospA fusion protein. The disclosed monoclonal antibodies are raised by immunization with whole bacterial cell or with the recombinant antigenic proteins.

Fikrig, et al., *Science* 250:553–56 (1990), document the passive protection of mice (C3H/HeJ) with polyclonal sera to killed *B. burgdorferi* or to *E.coli* expressing ospA, or with an ospA-specific monoclonal antibody. The investigators also show that mice were actively protected upon immunization with a purified, recombinant ospA/glutathione S-transferase fusion protein. Protection was measured in terms of the immunogen's ability to prevent infection or to abrogate the histopathological manifestations of the disease.

Bergström, et al. (WO 90/04411), also suggest the possibility that immunogenically active *B. burgdorferi* fractions could be used in vaccines. No data are provided, however, to demonstrate either the immunogenicity or the protective efficacy of the disclosed fractions.

SUMMARY OF THE INVENTION

It is therefore an object of the present invention to provide an effective vaccine against Lyme disease in mammals and a method for vaccinating mammals against Lyme disease.

It is also an object of the present invention to provide a non-denaturing method for purifying *B. burgdorferi* proteins.

It is another object of the present invention to provide a diagnostic agent and a method using it for detecting the presence of a *B. burgdorferi* antibody in a body fluid.

In accomplishing these and other objects, there has been provided, in accordance with one aspect of the present invention, an immunogen comprising (a) an amount of a material selected from the group consisting of one or more serological forms of *B. burgdorferi* pC in homogenous form, a pC variant and a pC mimetic, the material having a structure sufficiently similar to native pC to induce the production of protective antibodies, and o (b) a physiologically-acceptable excipient therefor, wherein the immunogen is present in an amount sufficient to elicit an immune response that is protective of a susceptible mammal against Lyme borreliosis. In a preferred embodiment the immunogen further comprises an adjuvant, such as aluminum hydroxide.

In accordance with another aspect of the present invention, a method is provided for immunizing a susceptible mammal against Lyme borreliosis, comprising the step of administering to the mammal an immunologically effective amount of an immunogen as described above.

There has also been provided, in accordance with still another aspect of the present invention, a method of purifying B. burgdorferi proteins, comprising the steps of (a) disrupting a *B. burgdorferi* cell and fractionating the disrupted cell into membrane and cytoplasmic components; (b) resuspending the membrane component in a non-denaturing detergent thereby producing a solubilized protein and an insolubilized material and then separating said solubilized protein from said insolubilized material; (c) subjecting the solubilized protein to ion-exchange chromatography so as to produce protein fractions; and (d) assaying the protein fractions to identify those fractions which contain proteins of interest. Step (d) of this method may be followed by either hydroxylapatite chromatography and/or immobilized metal affinity chromatography so as to concentrate and further purify the proteins of interest.

In still another aspect of the present invention, a diagnostic agent for the detection of *B. burgdorferi* antibodies in a sample comprising a *B. burgdorferi* protein produced by the foregoing purification method is provided.

Finally, there has been provided a method of detecting the presence of *B. burgdorferi* antibodies in a sample, the method comprising incubating the sample with the above diagnostic agent, and detecting the presence of bound antibody resulting from the incubation.

DETAILED DESCRIPTION OF THE PREFERRED EMBODIMENT

Although several different *B. burgdorferi* antigens have been identified and characterized to varying degrees, pC protein has not been recognized heretofore as a protective agent against Lyme disease. A key aspect of this discovery was the recognition that for optimal protective potency it would be necessary to retain pC protein as close as possible to its original conformation. A novel method for producing homogenous pC protein has been developed, therefore, which leaves the native configuration of the protein substantially unaffected, enabling the use of pC as an immunogen against Lyme borreliosis. This non-denaturing purification method is applicable to the production of Borrelia antigens for use in the detection of Lyme disease.

The protective effect of non-denatured pC protein is readily demonstrated in the gerbil, which has not been recognized to date as a superior animal model for gauging the efficacy of a given antigen, such as pC, in raising protective antibodies against Lyme disease. Nevertheless, it has been found that the gerbil is particularly well suited for such evaluations, in part because borreliosis in gerbils mimics the disease in humans in several important aspects. Thus, in gerbils as in humans (1) the infection is multisystemic, affecting a variety of organs, such as skin, joints, nervous system, spleen, heart, bladder and kidney;

(2) the disease may be chronic. *B. burgdorferi* have been recovered from gerbils more than one year after challenge;

(3) swelling of the joints reminiscent of arthritis may develop in gerbils as in humans; and (4) a similar humoral immune response with respect to the specificity and the temporal development of the response. For instance, it has been discovered that infected gerbils and humans respond immunologically little if at all to ospA and ospB proteins. Indeed, in contrast to mice, ospA and ospB antibodies in gerbils and humans are rare.

Vaccine

One embodiment of the present invention relates to a vaccine against Lyme borreliosis, wherein the immunogen comprises the pC protein of *B. burgdorferi*. The pC protein is a cell-surface antigen, as demonstrated by proteolytic digestion of it from intact *B. burgdorferi* cells. It is further characterized as having a molecular weight of about 24 kd, although pC from different strains may show molecular weight and serological heterogeneity. By means of conventional hybridoma methodology, eleven monoclonal antibodies (*B. burgdorferi* monoclonal antibodies 22, 28, 29, 34–39, inclusive, 42 and 45) have been produced which bind with pC from *B. burgdorferi* strain Orth-1 and several other strains.

In addition, the complete DNA sequence (SEQ ID No: 1) and deduced amino acid sequence (SEQ ID NO: 2) for the *B. burgdorferi* pC protein used in protection studies is as follows:

| Pos | 1 | 2 | 3 | 4 | 5 | 6 | 7 | 8 | 9 | 10 | 11 | 12 | 13 | 14 | 15 | 16 | 17 | 18 | 19 | 20 | |
|---|---|---|---|---|---|---|---|---|---|---|---|---|---|---|---|---|---|---|---|---|---|
| 1 | Met | Lys | Asn | Thr | Leu | Ser | Ala | Ile | Leu | Met | Thr | Leu | Phe | Phe | Leu | Phe | Ile | Ser | Cys | Asn | 2 |
| 1 | ATG | AAA | AAT | ACA | TTA | AGT | GCG | ATA | TTA | ATG | ACT | TTA | TTT | TTT | TTA | TTT | ATA | TCT | TGT | AAT | 6 |
| 21 | Asn | Ser | Lys | Gly | Gly | Asp | Ser | Ala | Ser | Thr | Asn | Pro | Ala | Asp | Phe | Glu | Ser | Ala | Lys | Gly | 4 |
| 61 | AAT | TCA | AAA | GGG | GGT | GAT | TCT | GCA | TCT | ACT | AAT | CCT | GCT | GAC | TTT | GAG | TCT | GCG | AAA | GGA | 12 |
| 41 | Pro | Asn | Leu | Thr | Glu | Ser | Lys | Ile | Ile | Thr | Thr | Ser | Asn | Ala | Phe | Val | Leu | Leu | Ala | Val | 6 |
| 121 | CCT | AAT | CTT | ACA | GAA | AGC | AAA | ATA | ATT | ACA | ACA | TCT | AAT | GCA | TTT | GTA | CTG | CTG | GCA | GTT | 19 |
| 61 | Lys | Glu | Val | Thr | Leu | Ser | Ile | Ile | Glu | Asp | Glu | Leu | Thr | Lys | Ala | Thr | Ile | Ile | Gly | Lys | 8 |
| 181 | AAA | GAG | GTA | ACT | TTG | TCA | ATA | ATA | GAA | GAT | GAA | CTT | ACT | AAG | GCT | ACT | ATT | ATT | GGT | AAA | 24 |
| 81 | Lys | Ile | Gln | Gln | Asn | Ser | Leu | Gly | Asn | Asp | Lys | Lys | Ala | Glu | Lys | Ala | Ser | Leu | Lys | Ala | 10 |
| 241 | AAA | ATA | CAA | CAA | AAT | TCA | TTA | GGC | AAT | GAT | AAA | AAG | GCG | GAA | AAA | GCA | TCA | TTA | AAA | GCA | 30 |
| 101 | Gly | Tyr | Ala | Ile | Ser | Leu | Leu | Ile | Thr | Thr | Lys | Ala | Leu | Ala | Gly | Gly | Ser | Lys | Ser | Gly | 12 |
| 301 | GGA | TAT | GCA | ATA | TCA | CTA | TTA | ATA | ACC | ACA | AAA | GCA | CTT | GCA | GGA | GGA | TCA | AAA | TCA | GGA | 36 |
| 121 | Glu | Leu | Ala | Lys | Asp | Ser | Lys | Glu | Ile | Ala | Cys | Lys | Asp | Glu | Glu | Lys | Leu | Phe | Lys | Leu | 14 |
| 361 | GAA | CTT | GCA | AAG | GAT | TCA | AAG | GAA | ATT | GCA | TGT | AAA | GAT | GAA | GAA | AAG | TTG | TTT | AAA | CTA | 42 |
| 141 | Ala | Ala | His | Gln | Ala | Leu | Asp | Gly | Ile | Ala | Ala | Glu | Asp | Asn | Ala | Ala | Ala | Ser | Asn | Ala | 16 |
| 421 | GCT | GCA | CAT | CAA | GCA | CTT | GAT | GGA | ATA | GCA | GCG | GAA | GAT | AAT | GCA | GCT | GCT | TCA | AAT | GCA | 48 |
| 161 | Ile | Gly | Lys | Lys | Asn | Gly | Lys | Thr | Lys | Thr | Ala | Ala | Glu | Asp | Val | Asp | Lys | Ser | Lys | Leu | 18 |
| 481 | ATT | GGG | AAA | AAT | GGG | CAG | GGT | ACT | AAG | ACT | GCA | GCG | GAA | GAT | GTT | GAT | AAG | TCA | AAA | TTA | 54 |
| 181 | Ser | Lys | Ala | Ala | Ser | Leu | Lys | Lys | Gln | Ala | Ala | Gly | Ser | Ser | Asn | Asn | Lys | Val | Leu | Lys | 20 |
| 541 | TCA | AAA | GCA | GCA | TCA | TTG | AAA | AAA | CAA | GCA | GCA | GGA | AGC | TCA | AAT | AAT | AAA | GTT | CTT | AAA | 60 |
| 201 | Thr | Ser | Pro | Val | Glu | Ala | Lys | Lys | Pro | *** | | | | | | | | | | | 21 |
| 601 | ACA | AGT | CCT | GTT | GAA | GCA | AAA | AAA | CCT | TAA | | | | | | | | | | | 63 |

The pC protein of the present invention may comprise a mixture of different serological forms of naturally occurring pC protein. In addition to pC protein obtained from *B. burgdorferi* cells, as described hereinafter, recombinant pC, variants of the naturally-occurring molecule ("pC variants") and "mimetics"—compounds having mimotopes which mimic pC epitopes — can be employed.

The category of pC variants includes, for example, oligopeptides and polypeptides corresponding to immunogenic portions of the pC molecule and any non-proteinaceous immunogenic portions of the pC molecule. Thus, a variant is intended to include a polypeptide that is homologous to and retains the salient immunological features of the natural pC molecule. In this regard, "homology" between two sequences connotes a likeness short of identity indicative of a derivation of the first sequence from the second. For example, a polypeptide is "homologous" to pC if it contains an amino acid sequence which corresponds to an epitope recognized by pC specific antibodies or T-cells. Such a sequence may be only a few amino acids long and may be a linear determinant or one which arises when amino acids from separated portions of a linear sequence are spatially juxtaposed after protein folding or after being subjected to covalent bond modification. The amino acid sequences which are antigenic determinants for purposes of this invention can be ascertained, for example, by monoclonal mapping analysis techniques which are known in the art. See Regenmortel, *Immunology Today* 10: 266–72 (1989), and Berzofsky, et al., *Immunological Reviews* 98: 9–52 (1987). Assaying for this type of similarity can also be effected via a competitive-inhibition study in the case of antibodies or by T-cell proliferation.

Polypeptides which qualify as pC variants according to these criteria can be produced, pursuant to the present invention, by conventional reverse genetic techniques, i.e., by designing a genetic sequence based upon an amino acid sequence or by conventional genetic splicing techniques. For example, pC variants can be produced by techniques which involve site-directed mutagenesis or oligonucleotide-directed mutagenesis. See, for example, "Mutagenesis of Cloned DNA," in CURRENT PROTOCOLS IN MOLECULAR BIOLOGY 8.0.3 et seq. (Ausubel, et al. eds. 1989) ("Ausubel").

Other pC variants within the present invention are molecules that correspond to a portion of pC, or that comprise a portion of pC but are not coincident with the natural molecule, and that display the immunogenic activity of pC when presented alone or, alternatively, when linked to a carrier. A pC variant of this sort could represent an actual fragment of the natural molecule or could be a polypeptide synthesized de novo or recombinantly.

To be used in recombinant expression of pC or a pC variant, a polynucleotide molecule encoding such a molecule would preferably comprise a nucleotide sequence, corresponding to the desired amino acid sequence, that is optimized for the host of choice in terms of codon usage, initiation of translation, and expression of commercially useful amounts of pC or a desired pC variant. Also, the vector selected for transforming the chosen host organism with such a polynucleotide molecule should allow for efficient maintenance and transcription of the sequence encoding the polypeptide. The encoding polynucleotide molecule may code for a chimeric protein; that is, it can have a nucleotide sequence encoding an immunological portion of the pC molecule operably linked to a coding sequence for a non-pC moiety, such as a signal peptide for the host cell.

In order to isolate a DNA segment which encodes a pC molecule, total *B. burgdorferi* DNA can be prepared according to published methods. See, for example, Maniatis, et al., MOLECULAR CLONING: A LABORATORY MANUAL (Cold Spring Harbor Laboratories, N.Y. 1982); Baess, *Acta Pathol. Microbiol. Scand.* (Sect. B) 82:780–84 (1974). The DNA thus obtained can be partially digested with a restriction enzyme to provide a more or less random assortment of genomic fragments; an enzyme with a tetranucleotide recognition site, such as Sau3A (MboI), is suitable for this purpose. The fragments from such a partial digestion then can be size-fractionated, for example, by sucrose gradient centrifugation (see Maniatis, supra) or by pulsed field gel electrophoresis (see Anad, *Trends in Genetics*, November 1986, at pages 278–83), to provide fragments of a length commensurate with that of DNA encoding the pC molecule.

According to well-known methods described, for example, in Ausubel at 5.0.1 et seq., the selected fragments can be cloned into a suitable cloning vector. A DNA thus obtained could be inserted, for example, at the BamH1 site of the pUC18 cloning vector. Chimeric plasmids or phage, inter alia, produced by joining the size-selected fragments to the cloning vector can then be transformed into *E. coli* or other host cells, which are screened thereafter for expression of the encoded protein. A variety of methods can be used for screening libraries to identify a clone containing the pC gene. These methods include screening with a hybridization probe specific for pC, such as an oligonucleotide probe, or screening for pC antigen expression using a pC specific immunological reagent. The latter, for instance, may be accomplished by immunoblotting a library with anti-pC monoclonal antibodies or with a specific polyclonal antibody prepared from animals immunized with purified pC. Once a clone containing pC encoding DNA is identified in the library, the DNA can be isolated, the region encoding pC protein fully characterized (as by sequencing), and, subsequently, the DNA can be used to produce pC expression vectors suitable to the production of pC-active protein.

As noted previously, to provide an effective immunogen the structure of the recombinantly expressed pC protein should be sufficiently similar to that of native (non-denatured) pC so that the protein induces the production of protective antibodies. To this end, it is preferable to express pC-encoding DNA in such a way that intracellular proteolysis and aggregation of the expression product, in denatured form, are avoided. One way to avoid these problems is to recombinantly produce pC in a host-vector system that provides for secretion of pC from the host cell, preferably directly into the culture medium. One such system is provided by *Bacillus subtilis*. A suitable secretion vector can be constructed for *Bacillus subtilis* by linking the *B. amyloliquefaciens* α-amylase signal sequence, see Young, et al., *Nucleic Acid Res.* 11:237–49 (1983), to the Bacillus plasmid vector pUB110, as described by Ulmanen, et al., *J. Bacteriol.* 162: 176–82 (1985). According to this approach, the coding sequence for the foreign protein is cloned downstream of the promoter, the ribosome binding site and the signal sequence for α-amylase. Transcription and translation of pC is under control of the α-amylase promoter and translation machinery in this construct, and secretion of pC from the host cell is provided by the α-amylase signal sequence. Similar vectors for use in yeast have been described and the expression secretion of pC in yeast using these vectors could be achieved.

Yet another approach for expressing pC in a host-vector system which avoids proteolysis, aggregation and denaturation is the use of vaccinia virus as a vector capable of expression in a variety of mammalian host cells susceptible to vaccinia infection. This approach would entail preparing a recombinant vaccinia virus-derived vector in which the pC gene is placed under the control of a promoter, along with translation and secretion signals, suitable for expressing pC protein in a vaccinia-infected host. As described in U.S. Pat. No. 4,603,112, the plasmid also would comprise, 5' to the transcription control regions and 3' to the 3' termination and polyadenylation signals, flanking sequences which are conducive to homologous recombination into a wild-type vaccinia genome. When a construct of this sort is introduced into a vaccinia infected host cell, the flanking sequences direct recombination between the plasmid vector and the vaccinia virus, with the result that a cloned structural sequence (here, encoding pC) becomes part of, propagates with and is expressed with the vaccinia virus. Preferably, the region between the flanking sequences also contains a selectable marker, such that in the presence of selection medium only those cells containing recombined vaccinia virus (and, in the present context, the sequence encoding a pC-active polypeptide), will survive.

A recombinant vaccinia strain produced in this manner can be used to infect mammalian cells, such as Vero cells or CV1 cells, suitable for high density fermentative growth. The pC-active protein expressed in these cells during fermentation would be secreted into the fermentation medium, from which it would be purified via conventional methodology.

In addition to natural pC and pC variants the present invention comprehends compounds ("mimetics") which mimic pC epitopes ("mimotopes"). One example of a mimetic is an anti-idiotype antibody, that is, an antibody that is produced by immunizing an animal with an antibody which specifically binds to an epitope on an antigen. The anti-idiotype antibody recognizes and conforms to the combining site on the first antibody. Therefore, the shape of its combining site closely resembles the epitope which fit into the combining site of the first antibody. Because an anti-idiotype antibody has a combining site whose shape mimics the original antigen, it can be used as a vaccine to generate antibodies which react with the original antigen. See Fineberg & Ertl, *CRC Critical Reviews in Immunology* 7:269–284 (1987). Appropriate mimetics could be identified by screening with a pC antibody to detect which compounds bind thereto or could be produced by molecular modelling. See Morgan, et al., "Approaches to the Discovery of Non-Peptide Ligands for Peptide Receptors and Peptidases," in *Annual Reports in Medicinal Chemistry* (Academic Press 1989), at pages 243 et seq.

The vaccine of the present invention is intended for the immunization of a susceptible mammal, including a human being, against Lyme disease. The term "immunogen" means an antigen which evokes a specific immune response leading to humoral or cell-mediated immunity, in this context, to infection with Borrelia. "Immunity" thus denotes the ability of the individual to resist or overcome infection more easily when compared to individuals not immunized, or to tolerate the infection without being clinically affected.

The immunogen of the present invention may be further comprised of an acceptable physiological carrier. Such carriers are well-known in the art and include macromolecular carriers. Examples of suitable carriers in mammals include tuberculin PPD, bovine serum albumin, ovalbumin or keyhole limpet hemocyanin. The carrier should preferably be non-toxic and non-allergenic.

The immunogen may be further comprised of an adjuvant such as an aluminum compound, water and vegetable or mineral oil emulsions (e.g., Freund's adjuvant), liposomes, ISCOM (immunostimulating complex), water-soluble glasses, polyanions (e.g., poly A:U, dextran sulphate, lentinan), non-toxic lipopolysaccharide analogues, muramyl dipeptide, and immunomodulating substances (e.g., interleukins 1 and 2) or combinations thereof. The preferred adjuvant is aluminum hydroxide. Immunogenicity can also be enhanced in mammals which have received live attenuated bacterial vectors, such as Salmonella or Mycobacteria, or viral vectors like Vaccinia, which express a pC-active polypeptide.

Techniques for formulating such immunogens are well-known in the art. For instance, the immunogen of the present invention may be lyophilized for subsequent rehydration in an excipient such as saline or other physiological solution. In any event, the vaccine of the present invention is prepared by mixing an immunologically effective amount of pC with the excipient in an amount resulting in the desired concentration of the immunogenically effective component of the vaccine. The amount of immunogenically effective component in the vaccine will depend on the mammal to be immunized, with consideration given to the age and weight of the subject as well as the immunogenicity of the immunogenic component present in the vaccine. In most cases, an amount of the immunogenic component of the vaccine will be in the range of 1 to 100 micrograms per dose, and preferably will be in the range of 10 to 50 micrograms per dose.

In yet another embodiment of the present invention, the immunogen is comprised of pC, a pC variant or a pC mimetic and one or more other *B. burgdorferi* antigens.

The methods of preparation of vaccines according to the present invention are designed to ensure that the identity and immunological effectiveness of the specific molecules are maintained and that no unwanted microbial contaminants are introduced. The final products are distributed and maintained under aseptic conditions.

The method of immunizing a mammal against Lyme disease involves administering to the mammal an effective amount of the foregoing immunogen. Administration may involve any procedure well-known in the art. For instance, a suitable administration strategy may involve administering the above described vaccine to mammals which are known to be exposed to ticks bearing *B. burgdorferi,* approximately 6 months to 1 year prior to the time of known or anticipated exposure. Any immunization route which may be contemplated or shown to produce an appropriate immune response can be employed, in accordance with the present invention, although parenteral administration is preferred. Suitable administration forms include subcutaneous, intracutaneous or intramuscular injections or preparations suitable for oral, nasal or rectal administration.

Method of Purification

In another embodiment of the invention, a novel, non-denaturing method has been developed to purify a variety of *B. burgdorferi* antigens from a variety of *B. burgdorferi* strains. Antigens include, but are not limited to ospA, ospB, pC, the flagellum structural protein and proteins having approximate molecular weights of 21 kd, 56 kd, 60 kd, and 63 kd. These procedures represent an improvement over prior art methods which are either denaturing, are specific for only a particular type of antigen or achieve only partial purification. The preferred method of purification comprises the following steps:

(a) disruption of *B. burgdorferi* cells and fractionation by centrifugation into "membrane" and "cytoplasmic" components;

(b) extraction of the membrane fraction with a non-denaturing detergent followed by centrifugation to obtain a supernatant comprising solubilized protein and to remove insoluble material as a pellet; and (c) fractionation of solubilized antigens by ion-exchange chromatography (diethylaminoethyl or "DEAE"), adsorbed antigens being eluted with a NaCl gradient.

The purification method can include concentration and further purification of the antigens by:

(a) hydroxylapatitechromatography, adsorbed antigens being eluted by increasing the phosphate content of the buffer; and/or (b) immobilized metal-affinity chromatography, adsorbed antigens being eluted with imidazole.

Other elution methods known in the art include elution by a reduction in pH or by increasing concentrations of ammonium chloride, histidine or other substance with affinity for the chelated metal.

Cell disruption can be accomplished by lysing cells by shaking them in suspension in a cell mill with tiny glass beads, by sonication or in a French-press. Alternatively, antigens may be extracted directly from the cell-surface of the organism by exposing the cell to a detergent, by changing the ionic strength of the cell's environment or by slightly shifting the temperature. Alternatively, a starting material comprised of membrane blebs which are shed from cells may be used.

The extraction of the membrane fraction may be accomplished with a detergent which preferably has good solubilizing power, is non-denaturing and is compatible with ion-exchange chromatography. The preferred detergent is zwitterionic detergent 3–14 by Calbiochem, although any detergent or organic solvent may be used which has the above characteristics. The detergent is typically used at a concentration of 1% (w/v) but would be effective to varying degrees in the range of 0.01–10% (w/v). Detergent extraction is carried out at a temperature in the range of 0° to 60° C., preferably at 37° C. and should take from ten minutes to 8 hours, preferably one hour. Chaotropic agents such as urea could be used in addition to the detergent to improve the solubilization process.

The detergent solubilized antigens are then fractionated by DEAE-chromatography. Preferably, a DEAE ion-exchange resin is used but other anionic or cationic exchange resins may be used instead or in conjunction with one another. In accordance with the present invention, an ion-exchange resin comprises an insoluble matrix to which charged groups have been coupled. Functional groups used for anion exchangers include amino ethyl (AE), diethylaminoethyl (DEAE) and quaternary aminoethyl (QAE) groups. Cation-exchangers may have carboxymethyl (CM), phospho- or sulphopropyl (SP) groups. Although samples are applied to the column in a Tris buffer containing zwitterionic detergent 3–14 (1%), and the antigens are eluted with a gradient of NaCl, other formulations may be equally effective.

Antigens may be concentrated by binding them onto hydroxylapatite, according to methods well known in the art. An alternative or complementary procedure by which antigens can be further concentrated/purified is by immobilized metal-affinity chromatography. This latter method is preferred to hydroxylapatite chromatography for the purification of pC since a better separation from ospA and B is achieved.

The advantage of the above described non-denaturing purification process is that the 3-D conformation of the protein is maintained, thereby keeping all the antibody combining sites found on the native protein, including those involved in protection. If a protein is denatured, the binding sites may be partially or completely destroyed and the antigen's capacity to induce antibodies to the antigenic sites will be correspondingly diminished. Proteins thus altered would therefore be unsuitable for use in vaccines.

An advantage of the above purification method over the whole-cell method, such as that taught by Johnson (1988), is that it produces homogenous protein free of any toxic components, thereby reducing the likelihood of an adverse reaction. "Homogenous" in this context means that at least 80% (w/v) of the protein is fully intact pC, with nearly all of the remainder represented by pC breakdown products. Thus, impurities in the form of media constituents and other Borrelia proteins are present, if at all, only in trace amounts. Homogenous pC may be comprised of more than one serological form of pC.

In this way the present invention enables the removal of unwanted, potentially immunogenic proteins which could induce autoantibodies and cause harmful autoimmune reactions in the immunized mammal. By the same token, the above-described purification method also ensures lot-to-lot reproducibility during vaccine production.

Protection

Based on discovered validity of gerbils as an animal model in this regard, experiments were conducted to confirm that immunity against *B. burgdorferi* infection could be imparted. These experiments are discussed in Example 3 below. Although ospA, ospB, pC, 63 kd outer surface protein, 21 kd and 94 kd proteins from *B. burgdorferi* strain Orth-1 were also tested, only pC protein showed clear signs of protective effect.

Method of Detection

Antigens prepared by the foregoing purification procedure are suitable for use in diagnostic tests, such as for the detection of antibodies to *B. burgdorferi* in body fluid from mammals. For instance, a non-denatured, homogenous protein produced by the foregoing method, may be incubated with a body fluid sample so as to detect the presence of bound antibody resulting from such incubation. The term "body fluid" is meant to include, but is not limited to cerebrospinal fluid, synovial fluid, urine, body cavity fluid, blood, serum, semen and saliva. Such tests, although well-known in the art, would be greatly improved by the sensitivity and specificity of the antigens purified according to the present invention.

The present invention is described in more detail in the following examples, which are illustrative and in no way intended to limit the scope of the invention.

Example 1: PROTEIN PURIFICATION

Preparation of membrane fractions

*Borrelia burgdorferi* cells were harvested by centrifugation (7000 g, 20 minutes, 4° C.) the cell pellet was washed twice in PBS-5 mM $MgCl_2$ and the cell wet-weight was determined. The washed cells were then resuspended in 100 mM Tris-HCl buffer, pH 7.5 (in the ratio of 1 g cells: 2 ml buffer) and the suspension was added to glass beads (0.17–0.18 mm diameter, 5 g beads for 1 g cell paste) in a metal beaker. The cells were then lysed by shaking the mixture in a Vibrogen® cell-mill (Model V14, Bühler ). Three minute cycles of shaking with cooling (4° C.) were repeated until lysis was greater than 99% complete, as assessed by dark-field microscopy. The lysate was then filtered on a sintered glass filter to remove the glass beads and the retained beads were washed with buffer to improve the yield of bacterial antigens in the filtrate.

The lysate was centrifuged for 20 minutes at 7500 g at 4° C. to produce a crude membrane fraction ("lsp"— low speed pellet). The supernatant was further centrifuged for 30 minutes at 100,000 g at 4° C. to produce the second membrane fraction ("hsp"— high speed pellet). Both membrane fractions were washed twice in 100 mM Tris-HCl buffer (pH7.5) using the original centrifugation conditions. Either membrane fraction could have been used as starting material for the purification of pC (or the other membrane associated antigens) but the hsp fraction contained fewer contaminating proteins.

Detergent extraction of membranes

Membranes were resuspended to about 10 mg protein/ml in a 10 mM Tris-HCl (pH7.5) buffer containing 1% (w/v) of the zwitterionic detergent 3–14 (Serva). After 1 hour of incubation at 37° C., the insoluble material was centrifuged out (100,000 g, 60 min., 4° C.).

DEAE ion-exchange chromatography

The detergent solubilized antigens were fractionated by DEAE chromatography, as exemplified below:

Column: PROTEIN-PAK® (CPLC column) DEAE 5PW semi-prep column (21.5 mm diameter, 150 mm long) from Waters.

Sample: 20 ml (4×5 ml) detergent solubilized antigen preparation (10 mg/ml).

Flow rate: 4 ml/min.

Buffer A: 10 mM Tris-HCl, pH7.5/1% (w/v) zwitterionic 3–14.

Buffer B: A+1 M NaCl.

Gradient: 0% B for 35 min., 0–30% B for 90 min., 30–65% B in 45 min., 65–100% B for 10 min.

The column was equilibrated with buffer A and the antigens eluted with increasing amounts of NaCl. To identify fractions containing the antigen of interest, aliquots of 8 ml fractions were precipitated with acetone and the pellets were analyzed by SDS-PAGE and/or immunoblotting.

Hydroxylapatite chromatography

Fractions enriched for the antigen of interest, such as pC, were pooled and dialysed against buffer C before being loaded onto the hydroxylapatite column. Bound antigen was eluted by increasing amounts of phosphate ions, e.g., with buffer D. In this way, dilute antigen solutions could be concentrated and further separation of the antigen from contaminants could be achieved. The technical specifications for this procedure are as follows:

Column: BIO-GEL® (Hydroxylapatite column) HPHT column (7.8 mm diameter, 100 mm long) from Bio-Rad.

Sample: pooled pC-containing fractions from the previous step (e.g., fractions 20–22) after dialysis against buffer C (4×5 ml).

Flow rate: 0.5 ml/min.

Buffer C: 10 mM MOPS-NaOH (3-N-morpholino). propanesulphonic acid), pH6.8/1 mM Na(PO$_4$)$^{3-}$/0.01 mM CaCl$_2$/1% (w/v) zwitterionic 3–14.

Buffer D: C+400 mM Na(PO$_4$)$^{3-}$.

Gradient: 0% D for 60 min., 0–100% D for 20 minutes.

The fractions were analyzed as described in the ion-exchange chromatography step.

Immobilized Metal-Affinity Chromatography

Fractions enriched for the antigen of interest, such as pC fractions from the DEAE ion-exchange chromatography separations, were pooled and the buffer adjusted (e.g., to ion-exchange chromatography fractions containing the pC protein NaCl was added to an end concentration of 150 mM). Filtered antigen solution (0.2 μm) was loaded onto the immobilized metal-affinity chromatography column (preloaded with Cu$^{++}$ as described by the manufacturer and equilibrated with buffer A), washed with buffer A and the bound antigen was eluted with the imidazole containing buffer B. In this way, dilute antigen solutions could be concentrated and further separation of the antigen from contaminants achieved.

The technical specifications for this procedure as exemplified for the pC protein are as follows:

Column: Chelating SUPEROSE® (Cross-linked agarose matrix) HR 16/5 column (16 mm diameter, 50 mm long) from Pharmacia/LKB.

Sample: pooled pC-containing fractions from DEAE ion-exchange chromatography with added NaCl (150 mM).

Buffer A: 20 mM Tris/Acetate pH7.5/150 mM NaCL/1% (w/v) zwitterionic detergent 3–14.

Buffer B: 20 mM Tris/Acetate pH7.0/150 mM NaCl/ 1%(w/v) zwitterionic detergent 3–14/50 mM imidazole Flow rate: 2 ml/min.

Gradient: A for 30 min., 0–100% B for 40 min.

The fractions containing pC were identified as in the ion-exchange chromatography step.

Example 2: RESULTS OF PURIFICATION PROCEDURE

Figure 1:
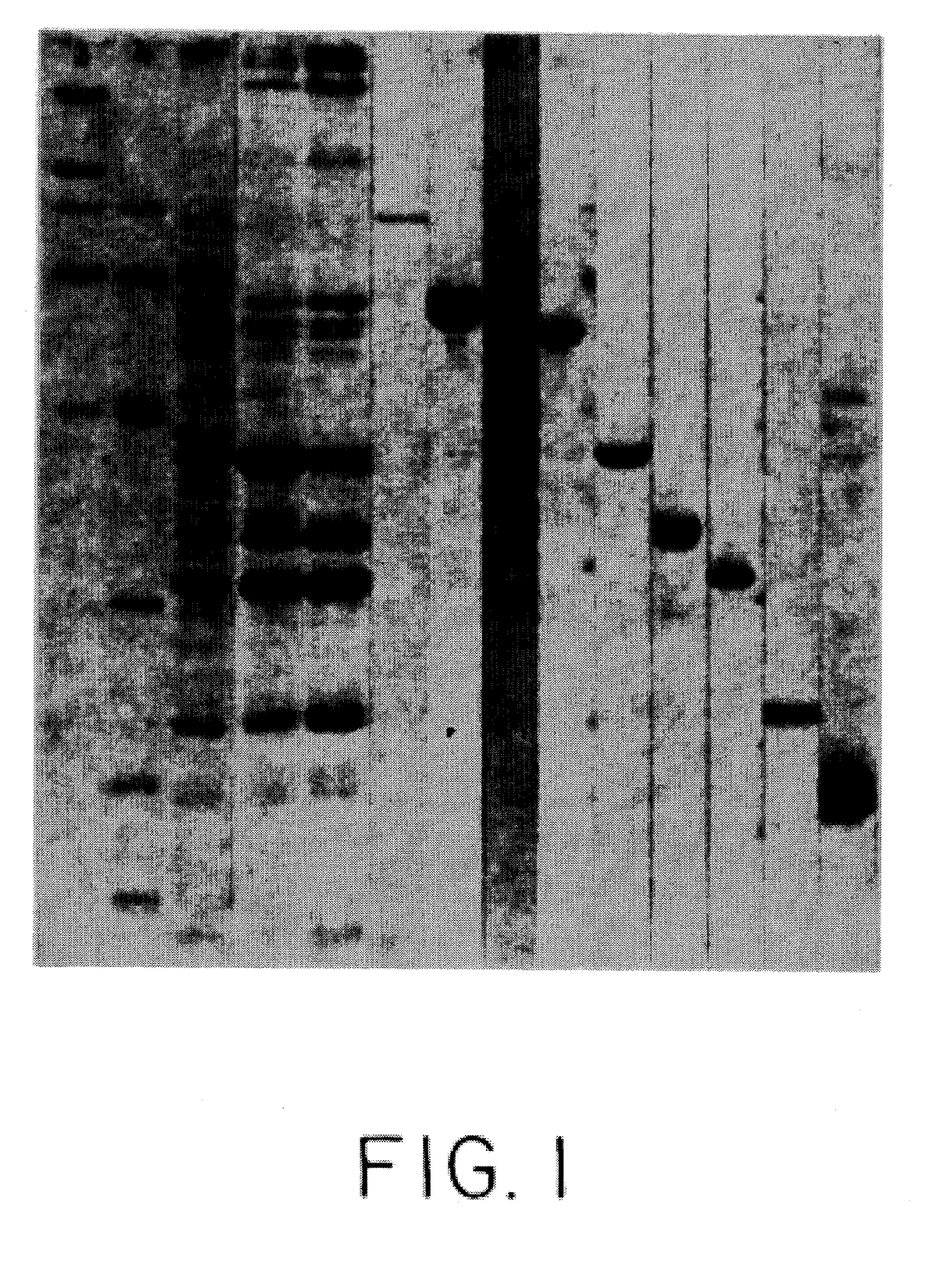
FIG. 1 is a photograph showing the results of electrophoretic analysis of antigens which have been purified from Orth-1 using the methods described herein.

The following antigens, prepared using the procedures outlined above, are characterized with reference to FIG. 1:

63 kd outer surface protein (lane 7)

60 kd protein (lane 8)

56 kd protein (lane 9)

flagellum structural protein (lane 10)

ospB (lane 11)

ospA (lane 12)

pC (lane 13)

21 kd protein (lane 14)

The first three steps of the purification process were essentially identical regardless of the protein being purified, although modifications could be introduced, if needed, to optimize separation. The hydroxyapatite chromatography step used in the purification/concentration of the pC protein is widely applicable, since almost all proteins of interest bind to the hydroxyapatite in buffer C.

Example 3: PROTECTION STUDIES

Because immunity acquired during an active infection is usually superior to immunity achieved through vaccination, a group of 10 gerbils were challenged intraperitoneally with $2\times10^7$ virulent *B. burgdorferi*, strain Orth-1, in order to show that protective immunity from Lyme borreliosis is a realistic goal. This dose was retrospectively estimated as being equivalent to approximately 1000 times the infectious dose required to infect 50% of the animals. Three weeks later, the animals were treated with antibiotics for one week to clear the infection. After a rest period of 17 days to allow time for the antibiotic to be cleared, the animals were re-challenged, as described above. Two weeks later, the animals were sacrificed and the bladder, spleen, kidneys and heart were cultured. All of these animals were protected in that *B. burgdorferi* could not be detected in any of the organ cultures despite regular inspection of the cultures over an eight week period. In contrast, 80% of the control gerbils which had not been given the initial "immunizing challenge" were infected. To ensure comparability with the test animals, these controls had also been treated with antibiotics. This confirmed that the protection in the study group was attributable to acquired immunity and not to persistence of antibiotics in the tissues.

In the next series of experiments, the protective potency of antigens purified by described methods from *B. burgdorferi* was evaluated. Gerbils were intraperitoneally immunized twice, with a two week interval between immunizations, with 10 μg amounts of aluminum hydroxide adjuvanted antigen. Two weeks after the final immunization, the animals were challenged intraperitoneally, together with a non-immunized control group, with $2\times10^7$ virulent *B. burgdorferi* strain Orth-1. Two weeks later, the animals were killed and the bladder, spleen, kidneys and heart were cultured for spirochaetes. Cultures were regularly inspected for 8 weeks.

OspA, ospB, pC and the 63 kd outer surface protein, all from the challenge strain Orth-1, were tested. Only the animals immunized with the pC protein showed clear signs of a protective effect. Although no absolute protection was shown, the infection in the pC immunized animals was less severe with fewer organs being infected. The heart and kidney cultures from the immunized animals were negative for *B. burgdorferi*, in comparison to the approximate 50% infection rate in the controls. Similarly, the infection rate in the spleen which was approximately 70%, was almost halved. Only with regard to the most susceptible organ, the bladder, was there no appreciable change in the number of infected cultures. OspA, ospB and the 63 kd protein were totally ineffective. The results of these experiments are set out in Table 1 below.

TABLE 1

| | | No. Infected gerbils/No. Tested | |
|---|---|---|---|
| Expt | Immunogen | Immunized | Controls[1] |
| 25 | live bacteria[2] | 0/10 | 4/5 |
| 20 | killed bacteria[3] | 6/10 | 10/10 |
| 23 | killed bacteria[3] | 7/8 | 10/10 |
| 30 | killed bacteria[3] | 8/9 | 10/10 |
| | | 21/27 | 30/30 |
| 33 | pC protein | 8/9 | 10/10 |
| 37 | ospB | 10/10 | 9/9 |
| 38 | 63kd osp | 10/10 | 9/9 |
| 41 | ospA | 10/10 | 10/10 |

[1]Control or non-immunized gerbils
[2]Challenged with live *B. burgdorferi*, antibiotic treated and re-challenged to assess protection, i.e., "natural immunity."
[3]Formalin killed B. burgdorteri (two 25 μg doses, calculated an protein)

A subsequent experiment was performed in accordance with the same protocol as described above was performed, except that the challenge dose was reduced to $10^6$ organisms. Upon immunization, pC provided unambiguous protection. By contrast, there was no evidence of protection following immunization with ospA, 21 kd or the 94 kd proteins. As shown in Table 2, all the gerbils immunized with pC showed protective effect whereas none of the gerbils immunized with ospA, 21 kd or 94 kd proteins showed much effect.

TABLE 2

| | | No. Infected gerbils/No. Tested | |
|---|---|---|---|
| Expt | Immunogen | Immunized | Controls[1] |
| 46 | pC protein | 0/10 | 9/10 |
| | 94kd protein | 8/9 | |
| 47 | ospA | 10/10 | 10/10 |
| | 21kd protein | 10/10 | |

[1]Control or non-immunized gerbils

Example 4: CHARACTERIZATION OF pC PROTEIN AS A LIPOPROTEIN

Figure 2:
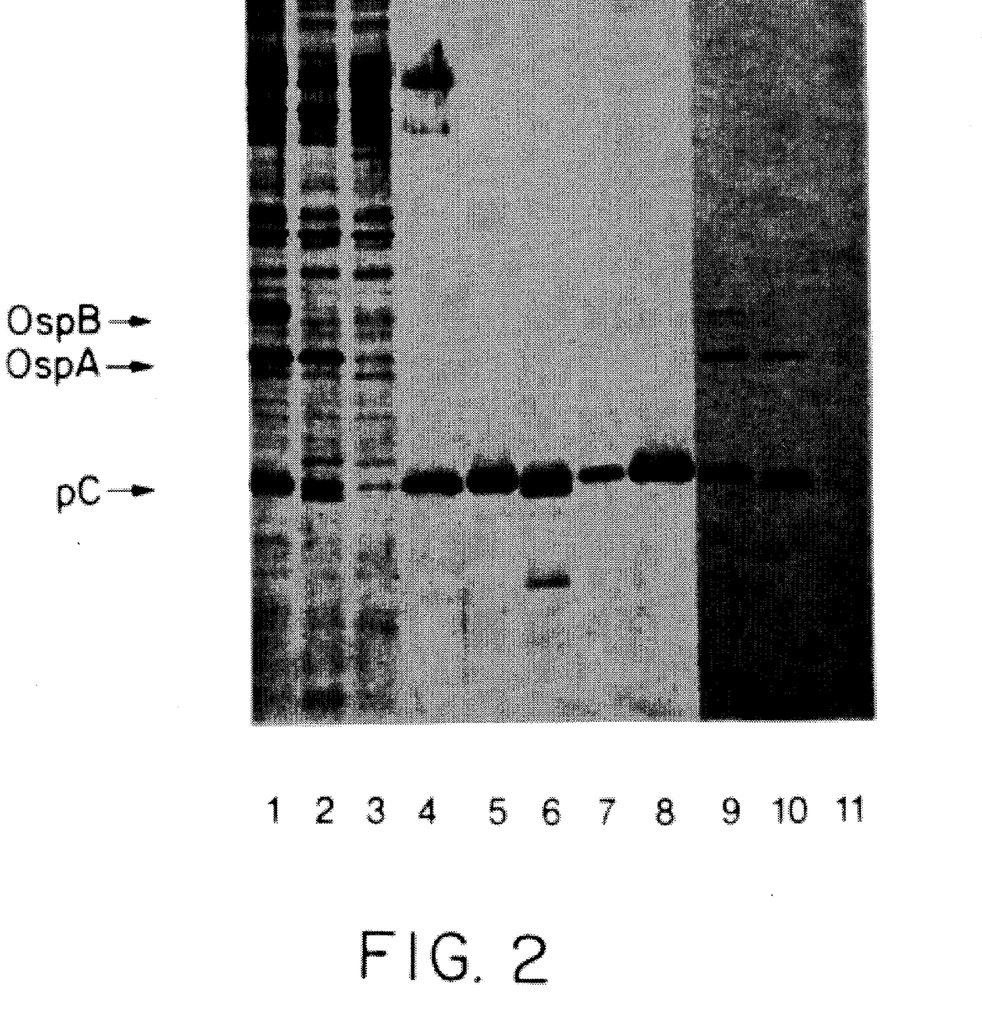
FIG. 2 is a photograph showing SDS-PAGE of *B. burgdorferi* cells incubated with trypsin (lanes 2, 6 and 10), proteinase K (lanes 3, 7 and 11) or without proteases (lanes 1, 5 and 9) in comparison with the purified pC protein (lanes 4 and 8). The electrophoretically separated proteins were characterized by gold staining with aurodye (lanes 1–4), by western blotting with a pC-specific monoclonal antibody (Mab35, lanes 5–8) and by fluorography for lipoproteins ($^3$H palmitic acid labelling, lanes 9–11).

*B. burgdorferi* grown in the presence of $^3$H palmitac acid incorporate this radioactively labelled fatty acid into their lipoproteins. These radiolabelled lipoproteins are separated by SDS-PAGE electrophoresis and identified by fluorography. One such lipoprotein identified from strain Orth-1 has the same apparent molecular weight (ca.24 kD) as the pC protein from this strain. When $^3$H palmitac acid radiolabelled whole-cells of *B. burgdorferi* Orth-1 were treated with trypsin and then analysed by SDS-PAGE, a characteristic double band corresponding to partially digested pC protein was seen. Western blotting of this material with pC specific monoclonal antibodies confirmed that these bands did indeed correspond to the pC protein. This doublet which is diagnostic for the pC protein was also detected on fluorographic analysis of the trypsin treated material. An analogous experiment using proteinase K which substantially reduces the amount of the cell-associated pC protein resulted in the almost complete loss of the 24 kD lipoprotein. These data, as shown in FIG. 2, confirm that the pC protein is a lipoprotein.

Methodological Details

Radiolabeling of *B. burgdorferi* cells: *B. burgdorferi* Orth-1 cells (3.5 ml of culture containing $1.6\times10^7$ cells/ml) were grown in BSK medium supplemented with radiolabelled palmitic acid (70 μl $^3$H palmitic acid, 55 Ci/mmol; 1 mCi/ml) for 48 hr at 33° C.), washed twice with PBS/5 mM $MgCl_2$ buffer and each aliquot was resuspended in 190 μl of the $PBS/MgCl_2$ buffer.

Proteolytic digestion: To 190 μl of cell-suspension was added 10 μl of either $PBS/MgCl_2$ (control), 62.5 μg trypsin in 1 mM HCl or 62.5 μg proteinase K in water. The samples were incubated with shaking at 25° C. for 50 min. (proteinase K) or 100 min. after which time 2 μl PMSF (50 mg phenylmethylsulphonylfluoride/ml in ethanol) was added. Cells were pelleted (10 min., 8000 g) and washed twice with 500 μl PBS/5 mM $MgCl_2$/0.5 mg/ml PMSF to remove digest products.

Analysis of samples: SDS-PAGE and western blotting were done using standard methods. Gels used for fluorography were incubated for 1 hr. in EN$^3$HANCE (NEN), washed for 30 min. with water, dried at 65° C. for 2 hr. and exposed using Hyperfilm MP (Amersham) at −80° C.

Example 5: EXPRESSION OF RECOMBINANT pC PROTEIN

DNA was extracted from *B. burgdorferi* Orth-1, partially digested with Sau 3A, size fractionated and cloned into the Bam H1 site of pUC18. Screening was conducted with an oligonucleotide hybridization probe and the detected gene was sequenced.

The pC gene was then amplified by PCR prior to cloning into a expression vector.

The PCR primers used were:

Primer 1 corresponding to the start of the pC open reading frame (the start codon is highlighted)

5' ATGAAAAAGAATACATTAAGTGCGATATTA 3' (bases 1–30 of SEQ ID NO: 1)

Primer 2 corresponding to the end of the pC open reading frame (the stop codon is highlighted)

5' ATTAAGGTTTTTTTGGAGTTTCTG 3' (SEQ ID NO: 3)

The PCR reaction was done following the manufacturer's instructions using VENT® DNA polymerase (New England Biolabs). Annealing of the primers to the template DNA (recombinant pUC18 plasmid with a *B. burgdorferi* derived DNA fragment containing the pC gene together with flanking DNA) was done at 57° C. and the primers were extended at 74° C. In total 25 cycles each of 1 min. were completed after which the sample was heated at 50° C. for 5 min.

The pC protein has been expressed as a maltose binding protein (MBP) fusion protein using a commercially available expression system (New England Biolabs ) .

Construction of the fusion plasmids

The PCR amplified pC gene was inserted downstream of the malE gene present on the expression vector plasmids pMAL-p2 and pMAL-c2 (100 ng of plasmid DNA was digested with restriction enzyme Xmn1 and ligated to 20 ng of the PCR product, i.e., pC gene). The ligated DNA was transformed into an α-complementing *E. coli* host (e.g., TB1 or DH5α) and clones containing the pC gene selected on LB agar containing ampicillin and X-gal. Insertion of the pC gene into the cloning vector, which confers ampicillin resistance, interrupts the male-lacZα fusion and results in a change in the colony phenotype (blue to white) under the chosen test conditions. Constructs with the pC gene in the correct orientation with respect to the tac promoter of the vector expressed a pC-MBP fusion protein as was confirmed by western blotting with pC specific monoclonal antibodies. The pC-MBP fusion protein was produced both with a signal peptide (pMAL-p2) which directs the fusion protein to the periplasm and without the signal sequence in which case the fusion protein remains in the cytoplasm (pMAL-c2). Cytoplasmic expression was higher than periplasmic expression but the latter has the potential advantage of yielding a soluble product.

Purification of recombinant pC

Crude extracts containing the periplasmic and cytoplasmic expressed pC-MBP were produced as described by the manufacturer. The fusion protein was purified by affinity chromatography by virtue of the specific binding of MBP to an amylose affinity resin. The MBP moiety is cleaved from the pC-MBP fusion protein leaving a complete pC protein because the fusion protein contains a single recognition site for the protease factor Xa adjacent to the start of the pC amino acid sequence. The MBP freed in this process together with any uncleaved fusion protein is removed by passage over the amylose resin (MBP binds but pC does not). Other methods known to be appropriate for the purification of pC could also have been used, e.g., ion-exchange chromatography, hydroxylapatite chromatography, immobilized metal-affinity chromatography.

According to this method, produced pC protein is complete. However, truncated forms of the pC protein (e.g., without the putative leader sequence) can also be produced by using the appropriate PCR primers.

---

What is claimed is:

1. A method of purifying *B. burgdorferi* pC protein comprising the steps of:

(a) disrupting *B. burgdorferi* cells and fractionating said disrupted cells into a membrane fraction and a cytoplasmic fraction;

(b) resuspending the membrane fraction in 0.1 to 10% (w/v) of a non-denaturing detergent thereby producing solubilized proteins and an insolubilized material and then separating said solubilized proteins from said insolubilized material;

(c) subjecting the solubilized proteins to ion-exchange chromatography so as to produce protein fractions;

(d) assaying the protein fractions to identify those fractions which contain the pC protein; and (e) subjecting the protein fractions which contain the pC protein to hydroxylapatite chromatography so as to concentrate and further purify the pC protein in a biologically active form.

* * * * *